United States Patent
Perricone

(10) Patent No.: US 8,580,742 B2
(45) Date of Patent: *Nov. 12, 2013

(54) TOPICAL GLUTATHIONE FORMULATIONS FOR MENOPAUSAL SKIN

(75) Inventor: Nicholas V. Perricone, Meriden, CT (US)

(73) Assignee: N.V. Perricone LLC, Meriden, CT (US)

( * ) Notice: Subject to any disclaimer, the term of this patent is extended or adjusted under 35 U.S.C. 154(b) by 636 days.

This patent is subject to a terminal disclaimer.

(21) Appl. No.: 12/718,706

(22) Filed: Mar. 5, 2010

(65) Prior Publication Data

US 2011/0218153 A1  Sep. 8, 2011

(51) Int. Cl.
 A61K 38/00 (2006.01)
 A61P 17/00 (2006.01)

(52) U.S. Cl.
 USPC ..................... 514/18.6; 514/18.7; 514/18.8

(58) Field of Classification Search
 None
 See application file for complete search history.

(56) References Cited

U.S. PATENT DOCUMENTS

| | | | |
|---|---|---|---|
| 3,984,569 A | 10/1976 | Kalopissis et al. | |
| 4,701,471 A | 10/1987 | Loucks, Sr. et al. | |
| 4,784,685 A | 11/1988 | Meister | |
| 5,376,361 A | 12/1994 | Perricone | |
| 5,382,679 A | 1/1995 | Galzigna | |
| 5,409,693 A | 4/1995 | Perricone | |
| 5,464,825 A | 11/1995 | Anderson et al. | |
| 5,472,698 A | 12/1995 | Rawlings et al. | |
| 5,516,507 A | 5/1996 | N'Guyen et al. | |
| 5,545,398 A | 8/1996 | Perricone | |
| 5,554,647 A | 9/1996 | Perricone | |
| 5,574,063 A | 11/1996 | Perricone | |
| 5,624,955 A | 4/1997 | Nagasawa et al. | |
| 5,643,586 A | 7/1997 | Perricone | |
| 5,709,868 A | 1/1998 | Perricone | |
| 5,879,690 A | 3/1999 | Perricone | |
| 5,928,654 A * | 7/1999 | Duranton ..................... | 424/401 |
| 6,011,067 A | 1/2000 | Hersh | |
| 6,030,948 A | 2/2000 | Mann | |
| 6,191,121 B1 | 2/2001 | Perricone | |
| 6,197,751 B1 | 3/2001 | Malinda et al. | |
| 6,296,861 B1 | 10/2001 | Perricone | |
| 6,437,004 B1 | 8/2002 | Perricone | |
| 6,602,519 B1 | 8/2003 | Stevenson et al. | |
| 6,627,732 B1 | 9/2003 | Sakon et al. | |
| 6,821,524 B2 | 11/2004 | Marini | |
| 6,979,459 B1 | 12/2005 | Perricone | |
| 7,029,695 B2 | 4/2006 | Redelmeier et al. | |
| 2004/0147452 A1 | 7/2004 | Yu et al. | |
| 2005/0192229 A1 | 9/2005 | Perricone | |
| 2006/0063718 A1 | 3/2006 | Perricone | |
| 2006/0069036 A1 | 3/2006 | Perricone | |
| 2006/0089310 A1 | 4/2006 | Goldstein et al. | |
| 2006/0264360 A1 | 11/2006 | Girardi et al. | |
| 2007/0015698 A1 | 1/2007 | Kleinman et al. | |
| 2007/0093551 A1 | 4/2007 | Yu et al. | |
| 2007/0207222 A1 | 9/2007 | Yu et al. | |
| 2008/0050332 A1 | 2/2008 | Sivak | |
| 2008/0051369 A1 | 2/2008 | Uemura et al. | |
| 2009/0029944 A1 * | 1/2009 | Skinner ........................... | 514/62 |
| 2011/0160143 A1 * | 6/2011 | Perricone ..................... | 514/18.7 |
| 2011/0250157 A1 * | 10/2011 | Perricone ......................... | 424/62 |
| 2011/0293743 A1 * | 12/2011 | Perricone ..................... | 424/638 |

FOREIGN PATENT DOCUMENTS

| | | |
|---|---|---|
| CN | 1203073 A | 12/1998 |
| DE | 202005002324 U1 | 6/2006 |
| JP | 11263720 A | 9/1999 |
| JP | 2002047178 A | 2/2002 |
| WO | 0137788 A1 | 5/2001 |
| WO | 2004010968 A1 | 2/2004 |
| WO | WO 2005048972 * | 6/2005 |
| WO | 2009047728 A2 | 4/2009 |

OTHER PUBLICATIONS

"Jojoba oil", http://www.gits4u.com/agri/agri5jojoba.htm, accessed Sep. 19, 2012.*
Boskou, Olive Oil: Chemistry and Technology, 2006, chapter 4, pp. 41-72.*
Perluigi, et al.; "In Vivo Protection by the Xanthate Tricyclodecan-9-YL-Xanthogenate against Amyloid Beta-peptide (1-42)-induced oxidative stress"; Neuroscience 138:1161-1170 (2006).
Hawkins, et al.;"Clinical improvement to photoaged skin with conjugated linoleic acid (CLA): A novel cosmetic PPAR lipid for anti-aging benefits", Journal of the American Academy of Dermatology, C.V. Mosby, St. Louis, MO, US, vol. 56, No. 2, Feb. 1, 2007, p. AB95, XP005937048, ISSN: 0190-9622.
Bergamo Paolo et al: "Conjugated linoleic acid enhances glutathione synthesis and attenuates pathological signs in MRL/MpJ-Fas(lpr) mice", Journal of Lipid Research, vol. 47, No. 11, Nov. 2006, pp. 2382-2391, ISSN: 0022-2275.
International Search Report and Written Opinion of the International Searching Authority; PCT/US2010/055969; Dec. 27, 2010; 12 pages.
Pensalfini et al: "Protective effect of new S-acylglutathione derivatives against amyloid-induced oxidative stress", Free Radical Biology and Medicine, Elsevier Science, US, vol. 44, No. 8, Feb. 9, 2008, pp. 1624-1636, XP022575894.

* cited by examiner

*Primary Examiner* — Noble Jarrell
(74) *Attorney, Agent, or Firm* — St. Onge Steward Johnston & Reens LLC

(57) ABSTRACT

Topical compositions to address menopausal skin conditions comprise an effective amount of S-acyl glutathione derivative and a carrier. Methods for addressing menopausal skin conditions comprise applying a composition containing S-acyl glutathione derivative in a dermatologically acceptable carrier to skin tissue. The acyl group is a saturated or unsaturated aliphatic $C_{12}$-$C_{24}$ group, preferably an unsaturated $C_{16}$-$C_{24}$ group, most preferably an unsaturated $C_{18}$ group. In particularly preferred embodiments, the acyl group is a linoleoyl group.

15 Claims, No Drawings

TOPICAL GLUTATHIONE FORMULATIONS FOR MENOPAUSAL SKIN

FIELD OF THE INVENTION

The present invention relates to topical compositions to improve the appearance of menopausal skin. More specifically, the present invention relates to topical compositions comprising acyl derivatives of glutathione to address severe skin dryness, dullness, loss of elasticity, or lack of radiance or to prevent or retard the appearance of exaggerated lines and wrinkles or spider vessels or red blotchiness, all visible conditions of peri-menopausal, menopausal, or post-menopausal skin.

BACKGROUND OF THE INVENTION

Reduced glutathione, most commonly called glutathione or GSH, is a relatively small molecule found in animals and plants, having the following formula:

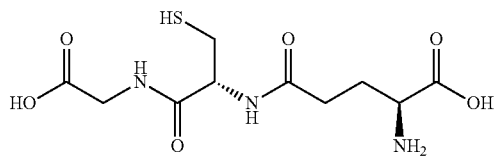 [SMILES: N[C@@H](CCC(=O)N[C@@H](CS)C(=O)NCC(=O)O)C(=O)O]

Glutathione is a water-phase orthomolecule. It is the smallest intracellular thiol molecule. It is a potent reducing compound due to its significant electron-donating capacity. Glutathione is a potent antioxidant and enzyme cofactor which plays a critical role in regulating cell activity.

Glutathione is a linear tripeptide of L-glutamine, L-cysteine, and glycine. Technically, N-L-gamma-glutamyl-cysteinyl glycine or L-glutathione, the molecule has a sulfhydryl (SH) group on the cysteinyl portion, which accounts for its strong electron-donating character. As electrons are lost, the molecule becomes oxidized, and two oxidized glutathione molecules become linked (dimerized) by a disulfide bridge to form glutathione disulfide or oxidized glutathione (GSSG). This linkage is reversible upon re-reduction. Glutathione is under tight homeostatic control both intracellularly and extracellularly. A dynamic balance is maintained between glutathione synthesis, its recycling from GSSG/oxidized glutathione, and its utilization.

Glutathione synthesis involves two closely linked, enzymatically controlled reactions that utilize ATP. First cysteine and glutamate are combined by gamma-glutamyl cysteinyl synthetase. Second, glutathione synthetase combines gamma-glutamylcysteine with glycine to generate glutathione. As glutathione levels rise, they self-limit further glutathione synthesis; otherwise, cysteine availability is usually rate-limiting. Fasting, protein-energy malnutrition, or other dietary amino acid deficiencies limit glutathione synthesis.

Glutathione recycling is catalyzed by glutathione disulfide reductase, which uses reducing equivalents from NADPH to reconvert GSSG to 2GSH. The reducing power of ascorbate helps conserve systemic glutathione. Glutathione is used as a cofactor by (1) multiple peroxidase enzymes, to detoxify peroxides generated from oxygen radical attack on biological molecules; (2) transhydrogenases, to reduce oxidized centers on DNA, proteins, and other biomolecules; and (3) glutathione S-transferases (GST) to conjugate glutathione with endogenous substances (e.g., estrogens) and to exogenous electrophiles (e.g., arene oxides, unsaturated carbonyls, organic halides), and diverse xenobiotics.

Free radical and other oxidative agents can deplete glutathione. The homeostatic glutathione redox cycle attempts to maintain glutathione levels as it is being consumed. Amounts available from foods are limited (less than 150 mg/day), and oxidative depletion can outpace synthesis.

The liver is the largest glutathione reservoir. The parenchymal cells synthesize glutathione for P450 conjugation and numerous other metabolic requirements, then export glutathione as a systemic source of SH/reducing power. Glutathione is carried in the bile to the intestinal luminal compartment. Epithelial tissues of the kidney tubules, intestinal lining, and lung, have substantial P450 activity and modest capacity to export glutathione.

Glutathione equivalents circulate in the blood predominantly as cysteine, the oxidized and more stable form of cysteine. Cells import cysteine from the blood, reconvert it to cysteine (likely using ascorbate as cofactor), and from it synthesize glutathione. Conversely, inside the cell glutathione helps re-reduce oxidized forms of other antioxidants such as ascorbate and alpha-tocopherol.

Glutathione is an extremely important cell protectant. It directly quenches reactive hydroxyl free radicals, other oxygen-centered free radicals, and radical centers on DNA and other biomolecules. Glutathione protects skin, lens, cornea, and retina against radiation damage, and the biochemical foundation of P450 detoxication in the liver, kidneys, lungs, intestinal epithelia, and other organs.

Glutathione is the essential cofactor for many enzymes which require thiol-reducing equivalents, and helps keep redox-sensitive active sites on enzymes in the necessary reduced state. Higher-order thiol cell systems—the metallothioneins, thioredoxins, and other redox regulator proteins—are ultimately regulated by GSH levels and the GSH/GSSG redox ratio.

Glutathione and its metabolites also interface with energetics and neurotransmitter syntheses, through several prominent metabolic pathways. Glutathione availability down-regulates the pro-inflammatory potential of leukotrienes and other eicosanoids.

Glutathione levels in human tissues normally range from 0.1 to 10 millimolar (mM), most concentrated in the liver (up to 10 mM) and in the spleen, kidney, lens, erythrocytes, and leukocytes. Plasma concentration is in the micromolar range (approx. 4.5 µM). Oxidative stressors that can deplete glutathione include ultraviolet and other radiation; viral infections; environmental toxins, household chemicals, and heavy metals; surgery, inflammation, burns, septic shock; and dietary deficiencies of glutathione precursors and enzyme cofactors.

A number of disclosures teach enhancing the cellular level of glutathione through administration of various glutathione derivatives. U.S. Pat. No. 5,464,825 (Anderson) discloses use of N-acyl monoalkyl glutathione monoester for increasing cellular levels in the liver and kidney cells to treat AIDS and other viral infections. U.S. Pat. No. 5,624,955 (Nagasawa) discloses glutathione prodrugs consisting of glutamyl cysteine derivatives to enhance glutathione level in the lens and prevent cataract onset. U.S. Pat. No. 7,029,695 (Redelmeier) discloses lipid formulations to enhance the bioavailability of analogs of glutathione for use in hematopoiesis modulation. Neuroscience 138:1161-1170 (2006) (Perluigi et al.) discloses use of Tricyclodecan-9-yl-xanthogenate to achieve an increase in glutathione levels in the neuronal cells to treat Alzheimer's disease WO 2009/047728 (Liguri) discloses that lipophilic derivatives of glutathione may be useful in treating Alzheimer disease and Huntington chorea.

Topical uses of glutathione derivatives have been disclosed. U.S. Pat. No. 3,984,569 (Kalopissis) discloses use of S-substituted linear and branched alkyl and alkenyl derivatives of glutathione for various scalp and hair applications and to combat excessive sebum secretion. U.S. Pat. No. 5,516,507 (N'Guyen) discloses glutathione mono-alkyl esters for topical treatment of cutaneous aging. These glutathione mono-alkyl esters are substituted at the glycine residue and employ alkyl chains having only 1 to 10 carbons. U.S. Pat. App. 2004/0147452 (Yu) proposes the use of non-amphoteric N-acyl glutathione derivatives for topical application for a broad range of conditions. The non-amphoteric derivatives of glutathione are proposed due to the instability of aqueous pharmaceutical formulations of mono and diester prodrugs of glutathione, which rapidly deteriorate over time.

U.S. Pat. No. 6,011,067 (Hersh) discloses compositions as adjuncts to topical therapy of desquamating inflammatory disorders, such as psoriasis, which compositions contain as active ingredients L-glutathione and a selenium compound. Hersh's disclosure stresses the importance of the presence of both ingredients to the anti-psoriatic effectiveness of the claimed composition.

My published applications, U.S. Patent Publications Nos. 20050192229, 20060063718; and 20060069036 disclose compositions with high glutathione concentrations for topical use in the treatment of psoriasis.

SUMMARY OF THE INVENTION

The present invention provides topical compositions to address conditions experienced by women in the menopausal state comprising a carrier and an effective amount of S-acyl glutathione derivative of the following formula:

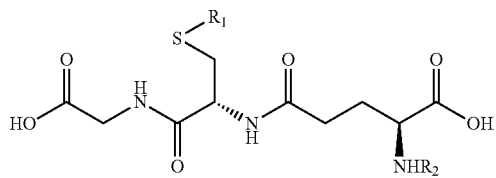

wherein $R_1$ is consists of a saturated or unsaturated aliphatic $C_{12}$-$C_{24}$ group, preferably an unsaturated $C_{16}$-$C_{24}$ group, more preferably an unsaturated $C_{18}$ group, most preferably, a linoleoyl group; and $R_2$ is a hydrogen, aliphatic or aromatic acyl group, preferably a hydrogen.

Methods for improving the condition, preventing or treating menopausal skin comprise applying a composition containing an effective amount of S-acyl glutathione derivative in a dermatologically acceptable carrier to skin.

More specifically, the present invention provides topical compositions and methods of applying compositions comprising acyl derivatives of glutathione to address severe skin dryness, dullness, loss of elasticity, or lack of radiance or to prevent or retard the appearance of exaggerated lines and wrinkles or spider vessels or red blotchiness, all visible conditions of peri-menopausal, menopausal, or post-menopausal skin.

DETAILED DESCRIPTION OF THE INVENTION

Aging of the skin is often caused by the loss of estrogen or decline in oestrogen associated with menopause. Oestrogen receptors are most abundant around the face, genital area and lower limbs. The present invention recognizes this process and provides a composition and method to minimize both prospective and existing skin conditions associated with loss of estrogen and oestrogen during menopause.

The term "skin" means the keratinous surfaces skin, hair and nails. The term "skin" when used herein is in the broad sense meaning the skin of the face, body, and neck as well as the lips.

The present invention comprises topical S-acyl glutathione (GSH) compositions to prevent skin aging and address skin conditions associated with menopause. The compositions help address severe skin dryness, dullness, loss of elasticity, or lack of radiance exaggerated lines and wrinkles or spider vessels or red blotchiness. These compositions may also be referred to using IUPAC nomenclature as S-alkanoyl glutathione compositions. The treatments consist of S-acyl glutathione derivatives of the formula:

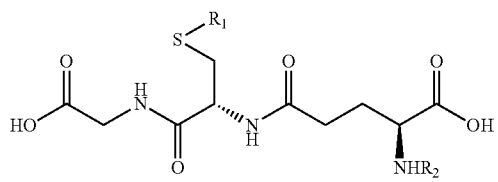

wherein $R_1$ is consists of a saturated or unsaturated aliphatic $C_{12}$-$C_{24}$ group, preferably a unsaturated $C_{16}$-$C_{24}$ group, preferably an unsaturated $C_{18}$ group; and $R_2$ is a hydrogen, aliphatic or aromatic acyl group, and most preferably a hydrogen group. In particularly preferred embodiments, $R_1$ is selected from the group consisting of linoleoyl or oleoyl groups, but is most preferably a linoleoyl group. The preferred embodiment of the invention is thus S-linoleoyl glutathione.

A particular object of the present invention is to provide S-acyl glutathione compositions having acyl groups to enhance skin penetration and transdermal absorption to improve the condition of the skin. The presence of the hydrocarbon chain of the apolar acyl group bonded to the glutathione thiol group enables the compounds of the invention to be effective as a topical application that can easily pass through the lipid bilayer of the cell membranes of epidermal and dermal cells. S-linoleoyl glutathione in particular has a lipophilic structure that makes it fat soluble and allows it to pass through cell membranes and be absorbed directly into cells.

S-acyl glutathione compounds of the present invention may be prepared by various means known to those of skill in the art. For example, enzymatic transthioesterification can be achieved by reacting glutathione with an appropriate acyl ester of coenzyme A (CoA) followed by purification from the water phase by HPLC or by chemically reacting glutathione with the corresponding acyl halide. See WO 2009/047728, supra, incorporated herein by reference. Another synthesis may be carried out by reacting the halide of the corresponding carboxylic acid with a solution of L-glutathione in trifluoroacetic acid under vacuum, adding ethyl acetate, and collecting the precipitated salt. See e.g. U.S. Pat. No. 3,984,569, supra, which is hereby incorporated by reference.

Topical compositions containing S-acyl glutathiones according to the present invention are intended to be topically applied to and absorbed by the skin tissue. S-acyl glutathiones activate transketolase, increasing its activity by 300%, and prevent protein glycation and AGE formation. After treatment for the recommended period of time, it is expected that decreased inflammation, irritation, and erythema of the skin will be observed, along with an increased skin elasticity and suppleness. Fine lines and wrinkles should be reduced and skin coloring should even out. The present invention thus is expected to prevent and treat skin aging, address skin dryness, dullness, loss of elasticity and lack of radiance. Particularly, treatments may be used to prevent or retard the appearance of spider vessels or red blotchiness associated with menopausal skin. In another embodiment, treatments may be used to prevent or retard exaggerated lines and wrinkles.

Only effective amounts of topical compositions containing S-acyl glutathione are needed to achieve the aforementioned benefits and prevent typical menopausal and aging effects on the skin. Generally, topical application to skin tissue is accomplished in association with a dermatologically acceptable carrier, and particularly one in which the S-acyl glutathione is soluble per se or is effectively solubilized (e.g., as an emulsion or microemulsion). Where employed, the carrier is inert in the sense of not bringing about a deactivation or oxidation of the glutathione derived active ingredient(s), and in the sense of not bringing about any adverse effect on the skin areas to which it is applied.

In one preferred practice of the invention, one or more S-acyl glutathione derivatives is applied in admixture with the dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin areas. While the carrier for the topical composition can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent(s). Many preparations are known in the art, and include lotions containing oils and/or alcohols and emollients vegetable oils, hydrocarbon oils and waxes, silicone oils, animal or marine fats or oils, glyceride derivatives, fatty acids or fatty acid esters, or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. In the preferred embodiment, the carrier is lecithin.

As noted, these ingredients can be formulated into a cream, lotion, or gel, or a solid stick, by utilization of different proportions of the ingredients and/or by inclusion of thickening agents such as gums or other forms of hydrophilic colloids. One possible embodiment is a solution used to saturate a pad used to wipe affected areas; another is a cleanser; and others are lotions, creams, and gels, which are referred to herein as dermally or dermatologically acceptable carriers, and are formulated using conventional techniques known to those of ordinary skill in the art. The term "topical composition" as used herein shall mean the complete product including the S-acyl glutathione active ingredient, the carrier, and any adjuvants, thickeners, excipients, etc. as described herein which is applied to a person's skin.

The quantity of S-acyl glutathione active ingredient in the carrier may be varied or adjusted widely depending upon the particular application, the potency of the particular compound or the desired concentration. Generally, the quantity of S-acyl glutathione active ingredient will range between 0.01% to 20% by weight of the topical composition, more preferably, 0.1% to 5% by weight. In some applications, the quantity of S-acyl glutathione active ingredient will exceed 5% by weight. In different embodiments, the weight percentage of S-acyl glutathione may be in the range of 0.01%-0.025%; 0.025%-0.05%; 0.05%-0.10%; 0.10%-0.50%; 0.50%-1.0%; 0.025%-0.50%; 0.025%-1.0%; 1.0%-2.0%; 2.0%-5.0%; 5.0%-10.00%; 1.0%-5.0%; 1.0%-10.0%; 10.0%-20.0%; 10.0%-30.0%; 10.0%-40.0%; 10.0%-50.0%; 10.0%-98.0%; 20.0%-30.0%; 20.0%-40.0%; 30.0%-40.0%; 30.0%-60.0%; 40.0%-50.0%; 40.0%-70.0%; 50.0%-60.0%; 50.0%-70.0%; 50.0%-80.0%; 60.0%-70.0%; 70.0%-80.0%; 80.0%-90.0%; or 90.0%-98.0%. Generally, lower concentrations of S-acyl glutathione active ingredients in a carrier are suitable, depending upon the application regimen and the active and adjunct ingredients employed.

Generally in the practice of methods of the invention, the topical composition is topically applied to the skin areas, such as that of the face, at predetermined intervals often as a moisturizer, tinted foundation, cleanser, toner, lotion, cream, or gel, it generally being the case that gradual improvement is noted with each successive application. Insofar as has been determined based upon clinical studies to date, no adverse side effects are encountered. It is an advantage of the invention that compositions of the invention do not require a pharmaceutical prescription.

The topical composition of the invention can contain additional ingredients commonly found in skin care compositions and cosmetics, such as, for example, tinting agents, emollients, skin conditioning agents, emulsifying agents, humectants, preservatives, antioxidants, perfumes, chelating agents, etc., provided that they are physically and chemically compatible with other components of the composition. Preservatives include, but are not limited to, $C_1$-$C_3$ alkyl parabens and phenoxyenthanol, typically present in an amount ranging from about 0.1% to about 2.0% by weight percent, based on the total composition. Emollients, typically present in amounts ranging from about 0.01% to 5% of the total composition include, but are not limited to, fatty esters, fatty alcohols, mineral oils, polyether siloxane copolymers, and mixtures thereof. Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. Emulsifiers, typically present in amounts from about 1% to about 10% by weight of the composition, include, but are not limited to, stearic acid, cetyl alcohol, stearyl alcohol, steareth 2, steareth 20, acrylates/C10-30 alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof. Antioxidants, typically present in an amount ranging from about 0.02% to about 0.5% by weight of the composition, include, but are not limited to, butylated hydroxy toluene (BHT); vitamin C and/or vitamin C derivatives, such as fatty acid esters of ascorbic acid, particularly ascorbyl palmitate; butylated hydroanisole (BHA); phenyl-α-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. As mentioned above, particularly preferred antioxidants are those that provide additional benefits to the skin such as ascorbyl palmitate.

Buffering agents are employed in many compositions. Preferably, the amount of buffering agent is one that results in compositions having a pH ranging from about 4.5 to about 8.5, more preferably from about 5.5 to about 8.5, most preferably from about 6.5 to about 8.0. Typical buffering agents are chemically and physically stable agents commonly found in cosmetics, and can include compounds that are also adjunct ingredients such as citric acid, malic acid, and glycolic acid buffers.

Some embodiments of this invention contain at least one other adjunct ingredient in addition to S-acyl glutathione. Adjunct ingredients include, but are not limited to one or more of: lipoic acid; α-hydroxy acids such as glycolic acid or lactic acid; ascorbic acid and its derivatives, especially fatty acid esters of ascorbic acid; or tocotrienols and tocotrienol derivatives and vitamin E compositions enriched with tocotrienols or tocotrienol derivatives. Additional ingredients and methods as disclosed in my U.S. Pat. Nos. 5,376,361; 5,409,693; 5,545,398; 5,554,647; 5,574,063; 5,643,586; 5,709,868; 5,879,690; 6,191,121; 6,296,861; 6,437,004; and 6,979,459, which are hereby incorporated by reference, may also be used.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method of treating spider vessels or red blotchy skin in peri-menopausal, menopausal, or post-menopausal skin comprising: applying to peri-menopausal, menopausal, or post-menopausal skin tissue having spider vessels or red blotchy skin, a composition comprising from 0.1% to 20% by weight of at least one S-acyl glutathione derivative of formula (I)

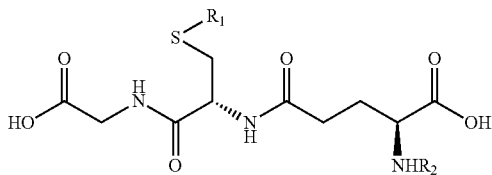

wherein R1 consists of a saturated or unsaturated aliphatic C12-C24 acyl group and R2 is a hydrogen; and a dermatologically acceptable carrier.

2. The method of claim 1 wherein R1 is an unsaturated C18 acyl group.

3. The method of claim 2 wherein R1 is a linoleoyl or oleoyl group.

4. The method of claim 1 wherein the carrier comprises lecithin.

5. The method of claim 1 wherein said composition further comprises one or more additional ingredients selected from the group consisting of: ascorbic acid and ascorbic acid derivatives; lipoic acid; α-hydroxy acids; and tocotrienols and tocotrienol derivatives and vitamin E compositions enriched with tocotrienols or tocotrienol derivatives.

6. A method of treating spider vessels or red blotchy skin in peri-menopausal, menopausal, or post-menopausal skin comprising: applying to peri-menopausal, menopausal, or post-menopausal skin tissue having spider vessels or red blotchy skin, a composition comprising from 0.1% to 20% by weight of S-linoleoyl glutathione of formula (II)

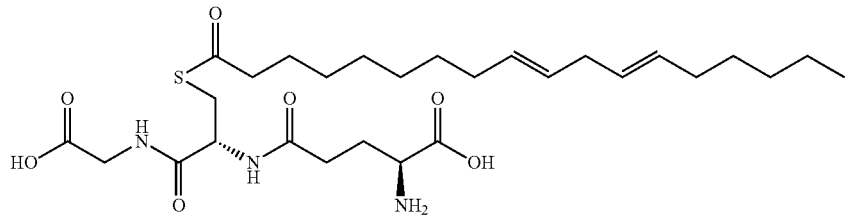

in a dermatologically acceptable carrier.

7. The method of claim 6 comprising between 0.1% to 5% by weight of S-linoleoyl glutathione.

8. The method of claim 6 comprising from 5% to 20% by weight of S-linoleoyl glutathione.

9. The method of claim 6 wherein said composition further comprises one or more additional ingredients selected from the group consisting of: ascorbic acid and ascorbic acid derivatives; lipoic acid; α-hydroxy acids; and tocotrienols and tocotrienol derivatives and vitamin E compositions enriched with tocotrienols or tocotrienol derivatives.

10. The method of claim 6 wherein the appearance of spider vessels or red blotchiness is improved.

11. The method of claim 1, wherein the composition is applied to spider vessels of peri-menopausal, menopausal, or post-menopausal skin.

12. The method of claim 1, wherein the composition is applied to red blotchiness of peri-menopausal, menopausal, or post-menopausal skin.

13. The method of claim 1 comprising between 0.1% to 5% by weight of S-acyl glutathione derivative.

14. The method of claim 1 comprising from 5% to 20% by weight of S-acyl glutathione derivative.

15. The method of claim 1 wherein the appearance of spider vessels or red blotchiness is improved.

* * * * *